United States Patent [19]

Skinner

[11] Patent Number: 5,071,349
[45] Date of Patent: Dec. 10, 1991

[54] MOUTH DAM

[76] Inventor: Gregory C. Skinner, 28398 Inverness Ct., Menifee, Calif. 92355

[21] Appl. No.: 615,130

[22] Filed: Nov. 19, 1990

[51] Int. Cl.⁵ .............................................. A61C 5/14
[52] U.S. Cl. .................................................... 433/136
[58] Field of Search ...................... 433/136, 140, 93; 604/385.1

[56] References Cited

U.S. PATENT DOCUMENTS

| | | | |
|---|---|---|---|
| 3,468,030 | 9/1969 | Peyser et al. | 433/136 |
| 3,705,585 | 12/1972 | Saffro | 433/136 X |
| 4,071,955 | 2/1978 | Julius | 433/136 |
| 4,501,586 | 2/1985 | Holtman | 604/385.1 X |
| 4,565,722 | 1/1986 | Highgate et al. | 604/385.1 |
| 4,657,539 | 4/1987 | Hasse | 604/385.2 |
| 4,813,872 | 3/1989 | Knitter | 433/136 |
| 4,820,155 | 4/1989 | Sauveur | 433/136 |
| 4,828,555 | 5/1989 | Hermansson | 604/385.1 X |
| 4,834,739 | 5/1989 | Linker, III et al. | 604/385.1 |
| 4,950,264 | 8/1990 | Osborn, III | 604/385.1 |

Primary Examiner—Robert P. Swiatek
Assistant Examiner—Nicholas D. Lucchesi
Attorney, Agent, or Firm—M. Reid Russell

[57] ABSTRACT

A mouth dam formed by cutting, punching or the like, each mouth dam from a sandwich of sheets of a thin, highly absorbing material, which sheets may be coated with a surfactant and further may include a flavor impregnated therein. Each mouth dam is cut, shaped or otherwise formed to be sealed at its edges, to have a length to width relationship where the length is three to four times the width, the width of the mouth dam ends is greater than at its center and the mouth dam sides slope uniformly from the center to the ends with an open area as a reservoir between the sealed mouth dam edges. A preferred mouth dam of the invention has a width at its ends that is from one-quarter (¼) to five-eights (⅝) of an inch and a length that is from one to one and three-quarters (1¾) inch.

6 Claims, 1 Drawing Sheet

U.S. Patent
Dec. 10, 1991
5,071,349
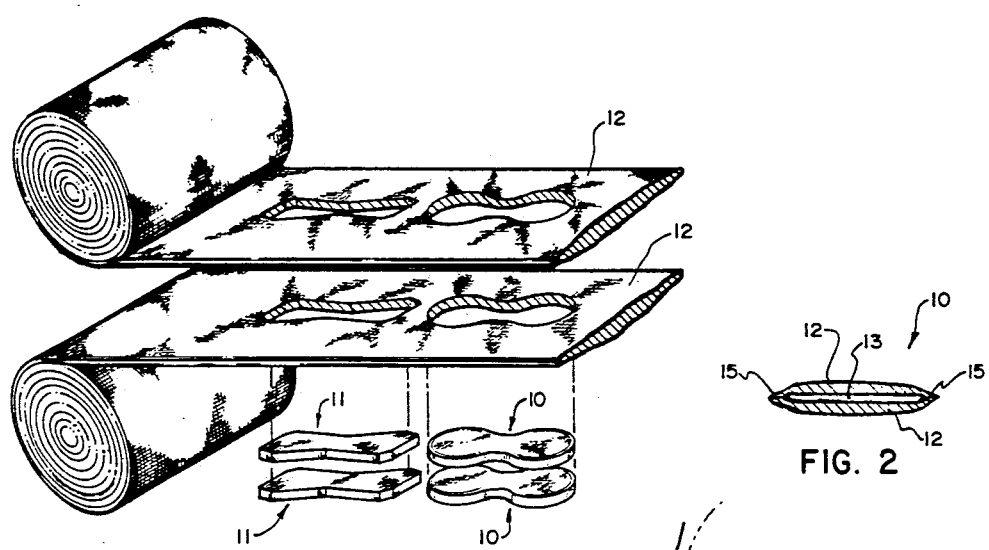
FIG. 1
FIG. 2
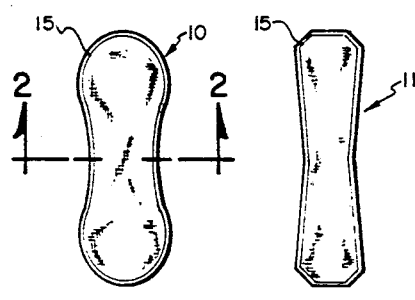
FIG. 1A FIG. 1B
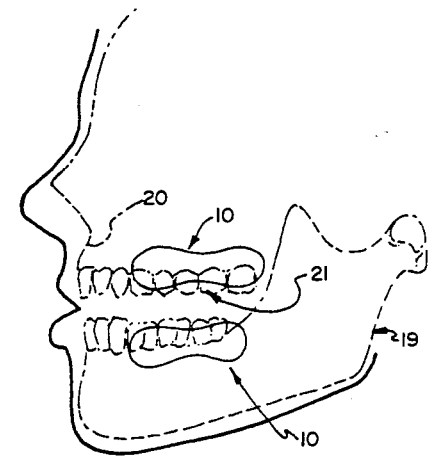
FIG. 3
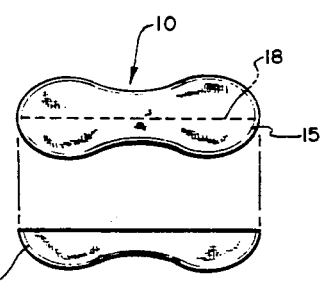
FIG. 3A
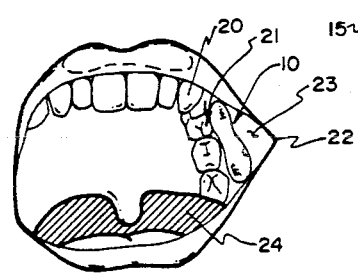
FIG. 4
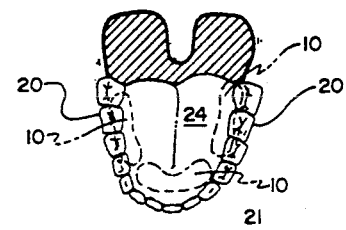
FIG. 5

MOUTH DAM

BACKGROUND OF THE INVENTION

1. Field of the Invention

This invention relates to liquid absorbing devices for placement in a dental patient's mouth for absorbing liquid including saliva and blood during the performance of a dental procedure.

2. Prior Art

It has long been common for a dentist in the performance of a dental procedure to install a cotton type sponge in a patient's mouth to absorb liquid from the field or area whereon the dentist works. Such sponges are generally compressed rolls of an absorbent cotton and are positioned alongside, over or adjacent to the patient's salivary ducts, against a patient's gingiva, or may be arranged next to the operating field.

Such cotton roll type sponge is intended to prohibit liquid from flowing or seeping onto the operating field, which field is generally a surface of a dental patient's tooth or their gingiva. A roll type sponge made from a stack of pads that are stitched together at their center longitudinal axis is shown in a patent to Julius, U.S. Pat. No. 4,071,955, and a similar roll sponge is shown in a patent to Wall, U.S. Pat. No. 4,372,314. Both of which sponges are essentially rolls. In practice, it has been found that round rolls often float out of position, and interfere with a dental procedure being performed. Accordingly, it is difficult to position and maintain in a dental procedure within the close confines of a patient's mouth.

Other sponges that are configured for placement at certain locations in a patient's mouth for collection of liquids are shown in patents to Saffro, U.S. Pat. No. 3,705,585 and Biggs, U.S. Pat. No. 2,613,441. Which devices are formed to fit in or on certain locations, are bulky and difficult to install, and are accordingly unlike the dam of the present invention. Like the present invention, certain early sponge arrangements have the value of a contoured and thin moisture absorbent device for use in a dental patient's mouth. Patents to Peyser et al, U.S. Pat. No. 3,468,030; Mattsson, U.S. Pat. No. 4,293,301; and an early Great Britain Patent to Nelicker, No. 816, recognize this need and each provides an arrangement that is essentially flat and is intended to fit within a mouth cavity. The shape of these devices, however, is unlike the present invention, and they do not provide for an effective absorbtion of moisture, and nor do they span a work area or field within a patient's mouth. Also, the Peyser et al device would not fit under a patient's tongue or in the areas adjacent thereto, nor would it fit in the front of a patient's mouth in the frenum area thereof. Additionally, the present invention lends itself to being folded longitudinally upon itself to fit within a narrow work area so as to be out of the way of the performance of a dental procedure.

Additional to dental sponges set out above, a number of arrangements of feminine hygiene appliances for absorbing liquids are available. Such patents have been issued for different types and shapes of sanitary napkins. Some examples of such arrangements are patents to: Johnson, U.S. Pat. No. 4,212,301; Johnson, Jr. et al, U.S. Pat. No. 2,964,039; Jurgensen, U.S. Pat. No. 2,064,431; Ahr, U.S. Pat. No. 4,321,924; Beyer Jr., U.S. Pat. No. 2,047,054 and Malfitano, U.S. Pat. No. 4,433,972; Hirschman, U.S. Pat. No. 3,983,873; and Denkinger, U.S. Pat. No. 3,905,372. None of which feminine hygiene patents teach arrangements that are structurally or functionally like the present invention.

SUMMARY OF THE INVENTION

It is the principal object of the present invention to provide a mouth dam that is formed as a sandwich of thin absorbent materials and has a contoured elongate shape to fit comfortably and conveniently within a dental patient's mouth to absorb liquid or moisture.

It is another object of the present invention to provide a mouth dam that is formed of a thin, highly absorbent material and has a contoured elongate shape to fit conveniently in a dental patient's mouth so as to present a minimum obstruction to a field or area therein whereon a dental procedure is being performed.

Still another object of the present invention is to provide a mouth dam that is formed of layers of a soft, flexible absorbent material.

Still another object of the present invention is to provide a mouth dam that is easily and inexpensively manufactured.

In accordance with the above objects, the present invention is in a mouth dam that is formed to have a flat contoured elongate shape that is punched or cut out of a sandwich of sections of an absorbent material. Such material can, for example, be a wood fiber and/or synthetic polypropylene fiber that is coated with a surfactant. One such material, that has been found in practice to be satisfactory for this use is known as COFORM TM that is manufactured by Kimberly-Clark. This material will absorb approximately fifteen (15) times its weight in liquid. Preferably, in such manufacture, a number of mouth dams of the invention are simultaneously punched out of section of overlying sheets so as stock to have an open area or reservoir between sealed edges. Each mouth dam has an elongate shape where the width dimension is between ⅛ and ¼ of its length dimension and is wider at its ends than at its middle.

The elongate mouth dam of the present invention is suitable for installation within a dental patient's mouth, to both span a work area, such as across one or more teeth, and to be stable when positioned between the gingiva and tongue area, or under the patient's tongue. So arranged, the mouth dam will absorb liquid such as is present during a dental procedure, and will prohibit that liquid from interfering with the work area whereon the dental procedure is being performed. Additionally, the mouth dam's elongate contoured shaped facilitates being longitudinally folded. So arranged, it is easily installed or inserted into a very narrow or close area, as between a dental patient's gingiva and cheek or in the frenum area of the mouth.

The elongate contoured shape of the mouth dam of the present invention allows it to be utilized, in either a flat or folded state, and be wedged into a narrow area so as to conform to that area, thereby minimizing a likelihood that it will move therefrom during the practice of a dental procedure.

BRIEF DESCRIPTION OF THE DRAWINGS

These and other objects and features will become apparent from the following detailed description in which preferred embodiments of the invention are described in detail in conjunction with the accompanying drawings.

FIG. 1 shows parallel rolls of flat, thin sheets of a highly absorbent material being layered together and two different embodiments of the invention in a mouth dam are shown being punched or cut therefrom;

FIGS. 1A and 1B,, are enlarged top plan views of the two embodiments of the mouth dams of FIG. 1;

FIG. 2 is a sectional view taken along the line 2—2 of FIG. 1A, showing the cross sectional area of the one embodiment of the mouth dam that includes an open reservoir between top and bottom layers;

FIG. 3 is a profile view of a patient's mouth area showing, in broken lines, the mouth cavity and teeth therein and showing two of the mouth dam embodiments of FIG. 1A arranged, respectively, between the patient's upper and lower gingiva areas and the inner surface of their cheek;

FIG. 3A shows the embodiment of the mouth dam of FIG. 1A folded along its longitudinal axis;

FIG. 4 shows a frontal view of a dental patient's mouth with their left cheek held out from the gingiva, and showing the folded mouth dam of FIG. 3A installed therein; and FIG. 5 shows the area of a dental patient's lower jaw wherein, two of the folded mouth dams of FIG. 3A are shown, in broken lines, installed within the mylohyoid area of the mouth between, under the patient's tongue and against their gingiva along both sides, and also shows a mouth dam of FIG. 1A arranged behind the patient's front teeth, in the frenum area, below the patient's tongue.

DETAILED DESCRIPTION OF THE INVENTION

FIG. 1 shows a perspective view of two embodiments of the present invention in a mouth dam 10 and 11, respectively, that have been punched, cut, or otherwise formed out of a flat sandwich of sheets of material 12 that are pressed together. The sheets of material 12, it should be understood, are preferably highly absorbent, flexible materials. One such preferred material is a combination of wood fibers and synthetic polypropylene fibers known as COFORM TM, that may be coated with a surfactant, and is manufactured by Kimberly-Clark. This material has been used in the manufacture of panty liners. COFORM TM is highly absorbent, possessing a liquid absorbency of approximately fifteen (15) times its dry weight. The preferred material 12 is commonly available in roll stock. To manufacture the present invention, it is preferred to overlay layers of material wound off from two rolls that are pressed together and mouth dams 10 and 11 are cut or punched out of the sandwich, as illustrated in FIG. 1.

FIGS. 1, 1A and 1B show two different embodiments of mouth dams, 10 and 11, of the invention, formed by cutting, punching, or like procedure, from a sheet of material 12. The mouth dams 10 and 11, respectively, are each examples of preferred embodiments of elongate contoured mouth dams of the present invention. Each such mouth dam has a width that is approximately ⅛ to ¼ the length dimension, and the width of the ends is greater than that of the longitudinal center. Therefore, with a preferred length dimension of approximately one (1) to one and three quarters (1¾) inches, the greatest mouth dam width will be one fourth (¼) to five eights (⅝) of an inch, with each mouth dam sloping outwardly from the center to a greater width at the ends. It should be understood, therefore, that each of the preferred mouth dam shapes shown in FIGS. 1A and 1B can be used, as set out below, to be folded longitudinally, as illustrated at broken line 18 in FIG. 3A. Longitudinally folding reduces by half that mouth dam width so as to facilitate its installation into close areas within a dental patient's mouth, as set out herein below with respect to a discussion of FIGS. 3, 4 and 5.

FIG. 2 shows a cross section of the mouth dam 10 of FIG. 1A illustrating that the cross section or thickness thereof is quite narrow with respect to the width and length dimensions and the device is sealed around its edge at 15 and includes an open area or reservoir 13 between the top and bottom sheets of material 12. FIG. 2 shows that the top and bottom sheets of material 12 of the mouth dam 10 are each fibrous to readily absorb and retain liquids passing into reservoir 13. Which liquid retention is enhanced by sealing the dam edges, as shown at 15 in FIG. 2, and in FIGS. 1A, 1B, and 3A. Preferably, the mouth dam 11 of FIG. 1B is similarly manufactured, and both the mouth dams 10 and 11 have their edges 15 pressed or rolled to seal that edge providing a reservoir 13 between the top and bottom sheets of material 12. Additional to the surfactant that is preferably included in the synthetic polypropylene fiber sheets 12, the top and bottom sheets of both the mouth dams 10 and 11 may also be coated or impregnated with a flavoring to increase the mouth dam acceptability by a patient, which flavoring, however, should not be such as to promote salivation.

FIG. 3 shows a mouth area 19 of a dental patient's head with the mouth cavity and teeth therein illustrated in broken lines at 20. The mouth dam 10 of FIG. 1A, is shown arranged in the mouth cavity, though it should be understood, the mouth dam 11 of FIG. 1B could be similarly used. Accordingly, a description of the functioning of mouth dam 10 should be taken as a description of the functioning of mouth dam 11 also. FIG. 3 illustrates that the mouth dam 10 of the present invention can be used in dental procedures involving either upper or lower teeth, to span across a number of teeth, and absorb liquid before it can flow into the work area or field 21. Such work area or field 21, for example, as shown in FIG. 3, can be the surface of the dental patient's upper teeth but, it should be understood, can as well be the surface of their lower teeth.

FIG. 4 illustrates a utilization of the mouth dam 10 that is installed in the left side of the patient's mouth between the gingiva of the upper teeth 20 and the inner surface of cheek 22. The cheek 22 is shown being pulled outwardly to expose, at 23, the left side of the mouth interior, with the mouth dam 10 shown fitted therein. The mouth dam 10 is shown conforming to and fitting snugly in area 23 of the patient's mouth, between their gingiva and cheek to keep the work area or field 21 dry while a dentist performs a dental procedure thereon.

FIG. 5 shows the lower jaw area of the dental patient of FIG. 3, with the work area or field 21 as being the surfaces of the teeth of the lower jaw. Three (3) mouth dams 10 of the present invention are shown in broken lines positioned along both sides and the front of the mouth, between the patient's inner gingiva surface and in the frenum and mylohyoid area beneath the patient's tongue 24. The mouth dams 10 arranged along the mouth sides are shown folded longitudinally and are positioned along the inner surfaces of the gingiva and teeth 20, fitting snugly within the mylohyoid area of the mouth. A third mouth dam 10, is also shown in broken lines, arranged in the mouth frenum area beneath the tongue 24 and against the inside of the patient's front teeth. The combination of the three mouth dams 10 provides for absorbing liquid that would accumulate around the patient's tongue during a dental procedure being performed on one or more of teeth 20.

The above discussion of the present invention in a mouth dam, additional to a description of the preferred mouth dam structure, also sets out different placements or positioning of the mouth dam 10 within a dental patient's mouth. From this discussion, it should be apparent that both the embodiments of mouth dams 10 and 11 will extend across one or more of the patient's teeth providing for an absorption of liquid on either side of that tooth as a barrier to liquid flowing or otherwise passing onto the work surface whereon the dental procedure is being performed. The elongate shape, and the particular width to length relationship of the embodiments of the mouth dams 10 and 11 and their inner reservoir 13 area, provide a dental practitioner with the ability to conveniently and effectively isolate his work area from a liquid contamination. Dental procedures, where the mouth dams 10 or 11 have been found to be effective for absorbing liquid include: the cutting of an amalgam preparation; crown and bridge preparation; surgical procedures; cementing of crowns, bridges, or the like; placement of amalgam or composite fillings; affixing sealants to the teeth; application of fluoride; and other isolation procedures. Particularly, the present invention is useful when it is arranged below a rubber dam that is installed in a patient's mouth so as to cover an area with a tooth to be worked on and fitted therethrough. Additionally, the present invention is suitable for use in procedures where an impression is taken in a dental patient's mouth. Such impression taking involves placement of a tray containing a viscous liquid impression material within that patient's mouth so as to fit over a number of the patient's teeth, one of which has been prepared to receive a crown. The impression material is allowed to set up around the teeth and the tray is then removed, leaving an impression of the patient's teeth in the solidified material. Such impression taking requires that the field or work area of the tooth or teeth whose impression is being taken, remain both clean and dry during the procedure. This necessitates that some liquid absorption device be utilized within the mouth during that impression taking procedure. Where a conventional round or roll type cotton sponge has been so used, it will often dislodge during the procedure and float on the impression taking material. The mouth dam of the present invention, arranged in either its flat or folded state, tends to fit snugly within a mouth cavity and, with the absorption of liquid, will even expand somewhat to fit more tightly therein.

In practice, it has been found that the above set out material known as COFORM TM, manufactured by Kimberly-Clark, is suitable for use as the sheets of material from which a mouth dam 10 or 11, each having a central reservoir 13 area, are formed. It should, however, be obvious that another material having similar absorption characteristics could be substituted therefor within the scope of this disclosure. Also, while the present disclosure has set out two embodiments of the mouth dam 10 and 11, it should be understood that, within the scope of this disclosure, the mouth dam of the present invention may be formed in any elongate shape so long as the length thereof is from three to four times greater than its width and the mouth dam is formed of sheets of a thin, absorbent material.

While preferred embodiments of the present invention in a mouth dam have been shown and described herein, it should be apparent that this disclosure is made by wa of example only and that variations are possible within the scope of this disclosure without departing from the subject matter coming within the scope of the following claims and reasonable equivalency thereof, which claims I regard as my invention.

I claim:

1. A mouth dam comprising a flat section that is formed as a sandwich from at least two layers of thin, liquid absorbent materials wherefrom the mouth dam is cut or punched so as to compress the layers together into a seal around the mouth dam edge and forming a reservoir between said layer edges, said mouth dam formed to have a contoured elongate shape sized to fit comfortably within a human mouth said reservoir having a like shape where the flat section length is approximately three (3) to four (4) times it width and the width at its ends is greater than at its center.

2. A mouth dam as recited in claim 1, wherein the flat section has a width at its ends of from one quarter ($\frac{1}{4}$) to five eights ($\frac{5}{8}$) of an inch and a length of from (1) to one and three quarter ($1\frac{3}{4}$) inches.

3. A mouth dam as recited in claim 1, wherein the flat section has a lesser width at its center as compared to its ends and the sides thereof slope uniformly outwardly from said center to said ends.

4. A mouth dam as recited in claim 1, wherein the individual layers of the sandwich of layers of thin, liquid absorbent materials are each a combination of wood fibers and synthetic polypropylene to hold a weight of liquid that is approximately fifteen (15) times its dry weight.

5. A mouth dam as recited in claim 1, further including coating each flat section layer with a surfactant.

6. A mouth dam as recited in claim 1, further including impregnating the individual layers of thin, liquid absorbing materials with a flavoring.

* * * * *